United States Patent [19]

Toda

[11] Patent Number: 5,395,985
[45] Date of Patent: Mar. 7, 1995

[54] NOVEL COMPOUND AND SEPARATING AGENT

[75] Inventor: Fumio Toda, Ehime, Japan

[73] Assignee: Daicel Chemical Industries, Ltd., Osaka, Japan

[21] Appl. No.: 206,449

[22] Filed: Mar. 4, 1994

Related U.S. Application Data

[62] Division of Ser. No. 30,058, Mar. 12, 1993.

Foreign Application Priority Data

Sep. 9, 1991 [JP] Japan .................. 3-227991

[51] Int. Cl.⁶ .................. C07C 33/28; C07C 33/48
[52] U.S. Cl. .................. 568/813; 568/717; 568/807; 568/808; 568/809; 568/810; 568/811
[58] Field of Search .............. 568/808, 813, 807, 715, 568/811, 810

[56] References Cited

U.S. PATENT DOCUMENTS

| | | | |
|---|---|---|---|
| 4,089,908 | 5/1978 | Kathawala | 568/813 |
| 4,223,172 | 9/1980 | Sabourin et al. | 568/812 |
| 4,467,102 | 8/1984 | Toda et al. | 568/813 |

Primary Examiner—Werren B. Lone
Attorney, Agent, or Firm—Flynn, Thiel, Boutell & Tanis

[57] ABSTRACT

A compound represented by the general formula (I) and a separating agent comprising the same:

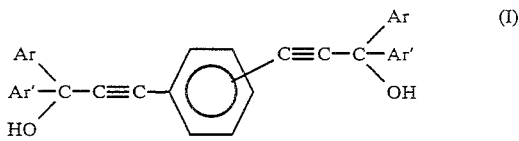

wherein Ar and Ar' are each an aromatic group; and the positional relationship of the two substituents on the central benzene ring may be any of ortho, meta and para.

The above compound is effective in the separation and purification of many compounds to and enables the provision of various compounds (such as intermediates of drugs) which are useful in the field of fine chemicals, particularly optically active substances, at high purities and in large amounts.

4 Claims, No Drawings

NOVEL COMPOUND AND SEPARATING AGENT

This is a division of Ser. No. 08/030 058, filed Mar. 12, 1993.

FIELD OF INDUSTRIAL APPLICATION

The present invention relates to a novel compound having a diethynylbenzene skeleton. The compound can be used for the separation of various mixtures which are otherwise difficult to separate and therefore can be utilized in the field of fine chemicals.

PRIOR ART

There have been known several substances (hereinafter called "host compounds") which have a property of combining with a separable compound (hereinafter called "a guest compound") contained in a mixture at a stoichiometric ratio to form a crystal (clathrate compound) and, therefore, have a capacity of separating the guest compound only from the mixture. Examples of such host compounds include compounds represented by the following formula (II):

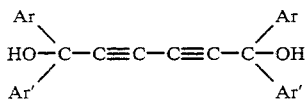

(wherein Ar and Ar' are each an aromatic group). Particularly when these host compounds are optically active substances, they are effective in the separation of optical isomers, which are generally thought to be extremely difficult to separate. However, the kinds of compounds which can be separated by these host compounds were limited.

DISCLOSURE OF INVENTION

An object of the present invention is to develop a novel host compound for the purpose of increasing the kinds of which compounds can be separated.

The present inventors have extensively studied to attain the above object. As the result, they have succeeded in developing a novel host compound which is different from those of the prior art with respect to the kinds of guest compounds, i.e., objects of separation, by modifying the diacetylene moiety of the host compound represented by the above formula (II) to thereby change the distance between the diarylhydroxymethyl groups present at both ends. The present invention has been accomplished on the basis of this success.

Thus, the present invention relates to a compound represented by the general formula (I) and a separating agent comprising the same:

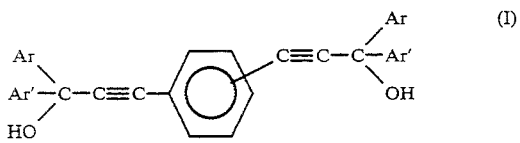

(wherein Ar and Ar' are each an aromatic group; the positional relationship of the two substituents on the central benzene ring may be any of ortho, meta and para).

In the general formula (I), aromatic groups represented by Ar and Ar' may be the same or different from each other and each aromatic group preferably has at most 10 carbon atoms. Examples of such an aromatic group include a phenyl group and α- and β-naphthyl groups and groups derived therefrom by substitution (such as an o-chlorophenyl group). The groups derived therefrom may be substituted by any substituents at any position, so far as the ability of the resulting compound as a host compound is not impaired. The structures and stereochemical characteristics of the diarylhydroxymethyl groups present at both ends have a great influence on the separating power of the host compound. When the compound represented by the general formula (I) is used for separation of chemically different substances, for example, that of a mixture of substances having boiling points close to each other or that of a mixture of diastereomers, the absolute configurations of both terminal groups in the case wherein Ar and Ar' are different from each other are not particularly limited, so that the compound may be a so-called mesoisomer wherein one of the terminal groups has R-configuration and the other has S-configuration, or may be a substance wherein both terminal groups have R-configuration, one wherein both terminal groups have S-configuration, an equivalent mixture of both substances, i.e., a so-called racemic modification, or a substance wherein Ar and Ar' may be the same. On the other hand, when the compound is used for the separation of optical isomers, which is a more sophisticated separation, the compound must be one wherein Ar and Ar' are different from each other and both terminal groups have either of R- and S-configurations, i.e., the compound must be optically active.

The compound represented by the above general formula (I) can be most easily prepared by conducting a double coupling reaction, as represented by the following reaction formula, in the presence of a transition metal catalyst, though it may be prepared by any process:

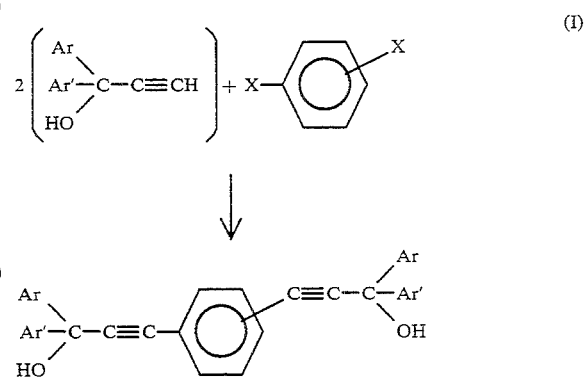

(wherein Ar and Ar' are each as defined above and X represents a halogen atom).

An optically active compound can be prepared from an optical isomer of a compound represented by the formula: ArAr'C(OH)C≡CH without troublesome separation, though it also may be prepared by conducting the above double coupling reaction by the use of a racemic modification of a compound represented by the formula: ArAr'C(OH)C≡CH and separating the obtained stereoisomeric mixture (with an optically active guest compound particularly in the separation of optical isomers). The optical isomer may be prepared by any of known processes, and the processes include, for example, those described in F. Toda et al., Isr. J. Chem., 25, 338 (1985) and in J. Chem. Soc., Chem. Commun., 743.

By utilizing the property of the compound (host compound) of the present invention represented by the above general formula (I) that the host compound combines with another compound (guest compound) to form a clathrate compound, the separation of the guest compound from a mixture and the purification of a third substance contaminated with the guest compound can be attained. The separation of the guest compound from a mixture and the purification of a third substance contaminated with the guest compound by the use of the host compound may be conducted by any suitable method.

Most generally, suitable amounts of a compound (a guest compound) which is an object of separation and the host compound are dissolved in a solvent; and a clathrate compound (a crystal comprising the host compound and the guest compound at a stoichiometric ratio) is precipitated from the obtained solution by any means selected from among temperature change, pressure change, evaporation of solvent, addition of poor solvent, and so on. Alternatively, a mixture which is an object of separation may be used as the solvent for the host compound. Further, when both guest and host compounds are solid, a clathrate compound is sometimes formed by mere blending. Furthermore, the purity, yield and crystal form of the clathrate compound can be controlled by conducting the crystallization under elevated pressure.

When the solid thus prepared exhibits physical properties (such as melting point and crystal form) different from those of each of the starting materials and comprises both starting material, is evident that a clathrate compound has been formed. Though the recovery of an objective compound from such a clathrate compound can be conducted by any of known processes, a process which comprises evaporating only a component having a lower boiling point into another vessel by vacuum distillation is the simplest and easiest one. Recrystallization of the clathrate compound is a suitable means for enhancing the purity of an objective compound, though an objective compound recovered from the clathrate compound may be recrystallized in some case.

Further, the formation of a clathrate compound is effective in the removal of unnecessary impurities.

Furthermore, when an optically active compound is selected from among those represented by the above general formula (I) to be used as a host compound, there is formed a clathrate compound containing, selectively, one of the optical isomers constituting an isomeric mixture of a guest compound, by which an optical isomer of the guest compound can be separated.

Generally, it is known that the interaction between a host compound and a guest compound occurs not only in a crystalline structure but also in a solution. Accordingly, gas or liquid chromatography can also be carried out by using a so-called stationary phase prepared by binding the host compound onto a support by chemical or physical means.

The host compound according to the present invention is different from known compounds represented by the above general formula (II) mainly in respect of the distance between the diarylhydroxymethyl groups, which is presumably the reason why the host compound of the present invention is effective in the separation of compounds which have been difficult to separate according to the prior art.

The host compounds of the present invention are effective in the separation and purification of more kinds of compounds, which enables the provision of various compounds (such as intermediates of drugs) which are useful in the field of fine chemicals, particularly optically active substances, at high purities and in large amounts.

EXAMPLE

The present invention will now be described by referring to the following Examples, though it is needless to say that the scope of the present invention is not limited by them.

In the Examples, Ph represents a phenyl group; He a methyl group; and Et an ethyl group.

EXAMPLE 1 synthesis of compound (p-I-1) (compound represented by the formula (I) wherein Ar is a phenyl group and Ar' is an o-chlorophenyl group):

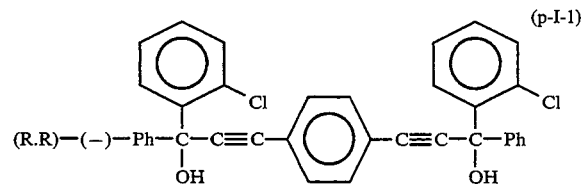

A mixture comprising 53.5 g (0.22 mol) of a compound ($[\alpha]_D = -139°$ (MeOH)) represented by the formula:

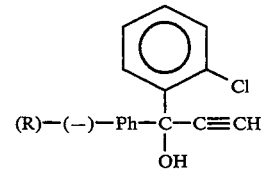

26.0 g (0.11 mol) of p-dibromobenzene, 0.1 g of $PdCl_2(PPh_3)_2$, 0.1 g of CuI, 0.52 g of $PPh_3$ and 280 ml of $Et_3N$ was heated under reflux for 4 hours.

The resulting mixture was cooled to a room temperature by being allowed to stand and filtered to remove crystalline $Et_3N \cdot HCl$ formed. $Et_3N$ in the liltrate was distilled out on an evaporator. 300 ml of ether was added to the residue and the obtained mixture was washed with diluted hydrochloric acid, water, aqueous sodium hydrogencarbonate and aqueous common salt successively, and dried over anhydrous magnesium sulfate. Acetone was added to the oily substance obtained by distilling out the ether to give a complex (melting point 81° to 82° C.) comprising the title compound (p-I-1) and acetone at a ratio of 1:2 as a crystal.

This crystal was heated in a vacuum of 1 to 2 mmHg at about 120° C. for 30 minutes to give 49.3 g (80.2%) of the title compound as a pale-yellow solid. This solid had an obscure melting point and exhibited an infrared absorption assignable to $\nu_{OH}$ (stretching vibration of hydroxyl group) at 3520 $cm^{-1}$ and 3400 $cm^{-1}$ and an optical rotation of $-82.6°$ (c=1.13, MeOH).

EXAMPLE 2 optical resolution of endo-tricyclo[5.2.1.0$^{2,6}$]-deca-3,8-dien-5-one (III)

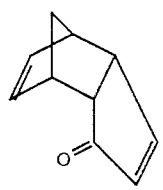

(III)

2.8 g (5.01 mmol) of (—)-(p-I-1) (At is a phenyl group and Ar' is an o-chlorophenyl group) and 1.47 g (10.1 mmol) of a racemic modification of the compound (III) were dissolved in 10 ml of toluene under heating. The obtained solution was allowed to stand at room temperature for 12 hours to precipitate 2.79 g of a clathrate compound comprising (—)-(p-I-1) and (+)-(III) at a ratio of 1:1 as a crystal. This crystal was recrystallized from toluene twice. 1.45 g of a pale-yellow crystal (melting point 116° to 118° C.) thus obtained was heated to 200° C. in a vacuum of 1 mmHg to give 0.30 g of (+)-(III) $\{[\alpha]_D = +140° \text{ (c=0.77, MeOH)}\}$.

EXAMPLE 3 resolution of γ-methyl-γ-butyrolactone (IV)

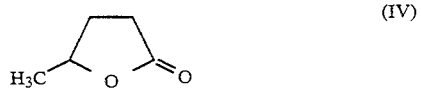

(IV)

3.02 g of (—)-(p-I-1) (At is a phenyl group and Ar' is an o-chlorophenyl group) and 2.16 g of racemic γ-methyl-γ-butyrolactone (IV) were dissolved in 10 ml of ether, followed by the addition of 5 ml of hexane. The resulting solution was allowed to stand at room temperature for 12 hours to give 2.8 g of a clathrate compound comprising (—)-(p-I-1) and (+)-(IV) at a ratio of 1:2 as a crystal. This crystal was heated to 200° C. in a vacuum to give 0.73 g of (+)-(IV) having an enantiomer excess (e.e.) of 29.1% $\{[\alpha]_D = +8.8° \text{ (c=0.64, MeOH)}\}$.

EXAMPLE 4 synthesis of compound (p-I-2) (compound represented by the formula (I) wherein Ar and Ar' are both phenyl groups):

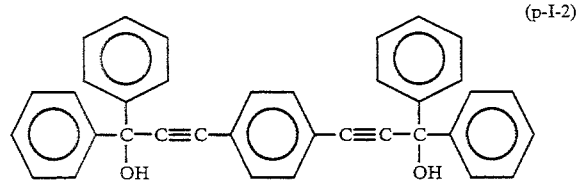

(p-I-2)

The title compound (p-I-2) was prepared from a compound represented by the formula:

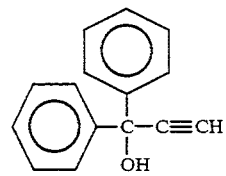

and p-dibromobenzene in the same manner as that of Example 1.

The obtained product had a melting point of 216° to 219° C. and exhibited an infrared absorption assignable to $\nu_{OH}$ at 3540 cm$^{-1}$.

EXAMPLE 5 synthesis of compound (m-I-1) (compound represented by the formula (I) wherein Ar is a phenyl group and Ar' is an o-chlorophenyl group):

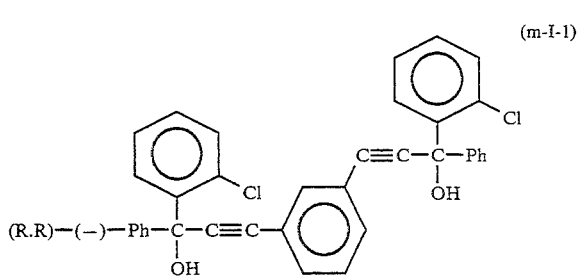

(m-I-1)

The title compound (m-I-1) was prepared from a compound represented by the formula:

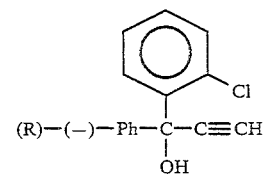

and m-dibromobenzene in the same manner as that of Example 1.

The obtained product had an obscure melting point and exhibited an infrared absorption assignable to $\nu_{OH}$ at 3300 cm$^{-1}$ and an optical rotation $[\alpha]_D$ of $-95.2°$ (c=1.0, MeOH).

EXAMPLE 6 synthesis of compound (m-I-2) (compound represented by the formula (I) wherein Ar and Ar' are both phenyl groups):

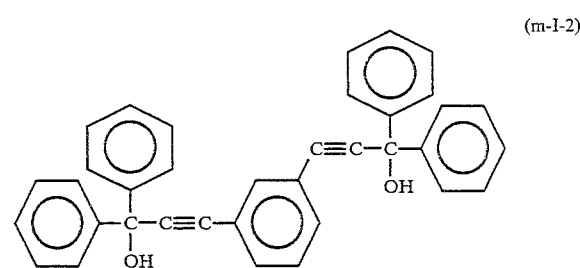

(m-I-2)

The title compound (m-I-2) was prepared from a compound represented by the formula:

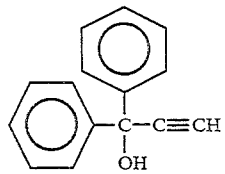

and m-dibromobenzene in the same manner as that of Example 1.

The obtained product had a melting point of 96° to 125° C. and exhibited infrared absorption assignable to $\nu_{OH}$ at 3230 cm$^{-1}$.

I claim:

1. A separating agent comprising a compound represented by formula (I):

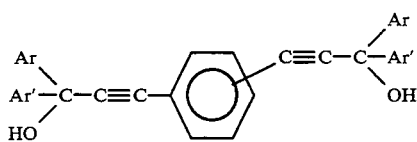

wherein Ar and Ar' are different from each other and are each an aromatic group selected from the group consisting of phenyl, naphthyl and chlorophenyl; and the positional relationship of the two substituents on the central benzene ring may be ortho, meta or para.

2. A method for separation or purification characterized by utilizing the property of the compound as set forth in claim 1 (host compound) of being combined with another compound a guest compound to form a clathrate compound to thereby separate the guest compound from a mixture or to thereby purify a third substance contaminated with the guest compound.

3. A method for separation characterized by utilizing the property of the compound as set forth in claim 1, a host compound being combined with only one of the optical isomers constituting an optical isomer mixture of a guest compound selectively to form a clathrate compound containing the optical isomer to thereby separate the optical isomers of the guest compound.

4. A method for separating an optical isomer from an optical isomer mixture characterized by binding the compound as set forth in claim 1 to a stationary phase by chemical or physical means to thereby conduct chromatography on this phase.

* * * * *

UNITED STATES PATENT AND TRADEMARK OFFICE
CERTIFICATE OF CORRECTION

PATENT NO. : 5,395,985
DATED : March 7, 1995
INVENTOR(S) : Fumio TODA

It is certified that error appears in the above-indentified patent and that said Letters Patent is hereby corrected as shown below:

On title page, insert the following:
---[22] PCT Filed: Aug. 27, 1992
---[86] PCT No.:    PCT/JP92/01083
          § 371 Date:    Mar. 12, 1993
          § 102(e) Date: Mar. 12, 1993---

Column 8, line 4; delete "another compound".
          line 10; after "compound" insert ---,---.

Signed and Sealed this

Second Day of January, 1996

Attest:

BRUCE LEHMAN

*Attesting Officer*   *Commissioner of Patents and Trademarks*